US008679797B2

(12) United States Patent
Yu et al.

(10) Patent No.: US 8,679,797 B2
(45) Date of Patent: Mar. 25, 2014

(54) METHOD FOR PREPARING GLUCAN AND MANNAN, GLUCAN PREPARATION AND MANNAN PREPARATION PRODUCED THEREBY AND USE THEREOF

(75) Inventors: Xuefeng Yu, Yichang (CN); Zhihong Li, Yichang (CN); Minghua Yu, Yichang (CN); Juan Yao, Yichang (CN); Yan Zhang, Yichang (CN)

(73) Assignee: Angel Yeast Co., Ltd. (CN)

( * ) Notice: Subject to any disclaimer, the term of this patent is extended or adjusted under 35 U.S.C. 154(b) by 332 days.

(21) Appl. No.: 12/990,206

(22) PCT Filed: Dec. 31, 2008

(86) PCT No.: PCT/CN2008/073895
§ 371 (c)(1),
(2), (4) Date: Oct. 28, 2010

(87) PCT Pub. No.: WO2009/132501
PCT Pub. Date: Nov. 5, 2009

(65) Prior Publication Data
US 2011/0045545 A1 Feb. 24, 2011

(30) Foreign Application Priority Data
Apr. 29, 2008 (CN) .......................... 2008 1 0105516

(51) Int. Cl.
| C12P 19/04 | (2006.01) |
| C12P 19/00 | (2006.01) |
| C12P 1/04 | (2006.01) |
| C12P 1/02 | (2006.01) |
| C12N 1/06 | (2006.01) |
| A01N 43/04 | (2006.01) |

(52) U.S. Cl.
USPC ............. 435/101; 435/72; 435/170; 435/171; 435/259; 514/54

(58) Field of Classification Search
USPC ............... 435/101, 72, 170, 171, 259; 514/54
See application file for complete search history.

(56) References Cited

U.S. PATENT DOCUMENTS

| 4,138,479 A | 2/1979 | Truscheit et al. | |
| 6,444,448 B1 * | 9/2002 | Wheatcroft et al. | ........... 435/101 |

FOREIGN PATENT DOCUMENTS

| CN | 1408879 A | 9/2003 |
| CN | 101012468 A | 8/2007 |
| JP | 2003-000262 A | 1/2003 |
| WO | 00/08201 A1 | 2/2000 |
| WO | WO 2006/121803 A1 | 11/2006 |

OTHER PUBLICATIONS

Yang, Cuizhu et al., "Study and applications of technology about breaking yeast cell wall," Food Science and Technology, No. 7, 2006, pp. 138-142, ISSN:1005-9989, pp. 139-140.
Zymolyase—20T Datasheet, AMS Biology, www.amsbio.com/datasheets/120491-1.pdf, retrieved on Jan. 27, 2012.
Supplementary European Search Report, Date Feb. 16, 2012, EP application No. 08874088.1-1521, 5 pages.
International Search Report mailed on Apr. 9, 2009, for International Application No. PCT/CN2008/073895 filed on Dec. 31, 2008, 3 pages.
Aguilar-Uscanga et at, "A study of the yeast cell wall composition and structure in response to growth conditions and mode of cultivation," Letters in Applied Microbiology, 2003, vol. 37, pp. 268-274.
Freimund et al., "A new non-degrading isolation process for 1,3-β-D-glucan of high purity from baker's yeast *Saccharomyces cerevisiae*," Carbohydrate Polymers, 2003, vol. 54, pp. 159-171.
Hu et al., "Isolation and Chemical and Physical Study of Yeast Glucans," Journal of East China University of Science and Technology, 1999, vol. 25, No. 5, pp. 477-479.
Huang et al., "Extraction of (1→3)-β-D-Glucan from *Saccharomyces Cerevisiae* and Study of the Mechanism," Fine Chemicals, 2003. vol. 20, No. 8, pp. 458-465.
Huang et al., "Research Progress in β-1,3-glucan from *Saccharomyces cerevisiae*," Liquor-Making Science & Technology, 2006, No. 12, pp. 100-103.
Huaxia et al., "Preparation and Physical-Chemical Properties of Alkali-Insoluble Glucan from Abolished Yeast," Guangzhou Food Science and Technology, 2004, vol. 20, No. 4, pp. 53-55.
Kwiatkowski et al., "A Study of *Saccharomyces cerevisiae* Cell Wall Glucans," J. Inst. Brew., 2009, vol. 115, No. 2, pp. 151-158.
Manners et al., "The Structure of a β-(1→3)-D-Glucan from Yeast Cell Walls," Biochem. J., 1973, vol. 135, pp. 19-30.
Science and Technology of Food Industry, 2007, vol. 28, No. 5, pp. 200-203.

* cited by examiner

*Primary Examiner* — Ganapathirama Raghu
(74) *Attorney, Agent, or Firm* — Kilpatrick Townsend & Stockton LLP

(57) ABSTRACT

The present invention provides a method for extracting glucan and mannan from the cell wall of a microorganism. Specifically, the method of the present invention in one embodiment comprises the steps of: a) treating the cells of the microorganism with an alkaline protease and an mannanase; b) separating the mixture from step a) into a heavy phase and a light phase; c) drying the heavy phase obtained from step b), obtaining the glucan preparation; and d) drying the light phase obtained from step b), obtaining the mannan preparation. Optionally, in the step c), the heavy phase obtained from step b) may be treated sequentially with an alkali and an acid, and separated again into a heavy phase and a light phase. The heavy phase is dried, obtaining the glucan preparation. The present invention further relates to the glucan preparation and mannan preparation produced thereby, and the uses thereof.

13 Claims, No Drawings

METHOD FOR PREPARING GLUCAN AND MANNAN, GLUCAN PREPARATION AND MANNAN PREPARATION PRODUCED THEREBY AND USE THEREOF

FIELD OF INVENTION

The present invention relates to the preparation of glucan and mannan. Particularly, the present invention relates to a method for preparing glucan and mannan from microorganisms, especially from yeasts. The present invention further relates to the glucan preparation and mannan preparation produced thereby, and use thereof.

BACKGROUND OF THE INVENTION

Currently, with the increasing incidence of cancer and the increasing concerns about antibiotic residual in animal feeds, researchers around the world are eager to find a safe and effective functional agent which improves the patients' immunity, so as to diagnose or treat diseases.

Cell-wall polysaccharides of microorganisms (especially yeasts) are regarded as a best choice. Upon entering the intestinal tract, the yeast glucan and mannan may be absorbed into the human body via intestinal epithelium through endocytosis, and play an effective role in enhancing the immunity of animal and human body, improving the intestinal function and resisting radiation. Its mechanism of action includes stimulating and activating macrophages, NK cells and other immunocytes, promoting the release of cytokines, and killing the tumor cells, antigens and other harmful particles directly or indirectly. In addition, they can adsorb various toxins in the intestinal tract due to their excellent capability of adsorbing, enhance the intestinal peristalsis and improve the intestinal function.

Glucan and mannan are the major components of microbial (particularly, yeast) cell walls. Glucan, as a glucose polymer, is an alkali insoluble polysaccharide with β-1,3-glucan as the backbone and minor β-1,6-detran as side chains. On the other hand, mannan is water soluble polysaccharide has α-1,6-bonded D-mannose as the backbone, with most or even all of the mannose molecules having side chains composed of 2-5 α-1,2- or α-1,3-linked mannose residues.

Multiple researches have been carried out regarding the extraction and utilization of cell wall glucan. However, these researches show several disadvantages: (1) the extraction method relates mainly to simple treatments with acid or alkali, and the glucan content of the preparations is lower than 60%; (2) substantial researches focus on the extraction of glucan, other than the simultaneous extraction of glucan and mannan (most of which is discarded); (3) some of the processes are not suitable for large-scale applications in industry, with low stability and yield.

In view of the diverse application of yeast cells in the fermentative industry and the various utilization of β glucan, novel methods for preparing glucan from yeast cells are needed in the art. These new methods shall overcome the disadvantages of low stability and/or low yield in the prior art.

BRIEF DESCRIPTION OF THE INVENTION

In one aspect, the present invention relates to a method for preparing glucan from microorganisms, comprising the steps of:

a) treating the cells of the microorganism with a protease and a mannanase;

b) separating the mixture obtained from step a) into a heavy phase and a light phase; and c) drying the heavy phase obtained from step b), thereby obtaining a glucan preparation.

In another aspect, the present invention relates to a method for preparing glucan and mannan from microorganisms, comprising the steps of:

a) treating the cells of the microorganism with a protease and a mannanase;

b) separating the mixture obtained from step a) into a heavy phase and a light phase;

c) drying the heavy phase obtained from step b), thereby obtaining a glucan preparation; and d) drying the light phase obtained from step b), thereby obtaining a mannan preparation.

Preferably, in the above methods, the heavy phase obtained from step b) may be treated sequentially with alkali and acid after step b), and separated again into a heavy phase and a light phase. Then the heavy phase obtained is subjected to the drying of step c), thereby obtaining the glucan preparation.

In another aspect, the present invention relates to a method for preparing mannan from microorganisms, comprising the steps of:

a) treating the cells of the microorganism with a protease and a mannanase;

b) separating the mixture obtained from step a) into a heavy phase and a light phase; and d) drying the light phase obtained from step b).

In some embodiments, the cells of the microorganism is selected from the group consisting of bacteria, fungi and plant cells, for example, yeast cells, such as cells of *Saccharomyces, Kluyveromyces, Candidas, Schizosaccharomyces* or *Hansenula*, most preferably the cells of *Saccharomyces*, such as *Saccharomyces cerevisiae* or baker's yeast.

In other embodiments, the cells are subjected to a pretreatment step that lyse autolyse the cells prior to step a).

In other embodiments, the protease used for the protease treatment is an alkaline protease, preferably proteases of *Bacillus subtilis*.

In other embodiments, the mannanase used for the mannanase treatment is selected from the group consisting of Gamanase™ (Novozymes), PURABRITE™ (Genencor International Inc.) or mannanase from Pangbo Biological Engineering Co., Ltd., Nanning, China, or any combination thereof.

The present invention further relates to the glucan preparation and mannan preparation produced according to the above methods.

The present invention further relates to the use of the glucan preparation and mannan preparation in the manufacture of food, nutrients, feed or cosmetics.

DETAILED DESCRIPTION OF THE INVENTION

Mannan is the polymer comprised of mannose units. In yeast, mannan binds both to the proteins on the outer surface of the yeast cell wall and to the inner cell membrane. Generally, the mannan accounts for 20-50% of the cell wall (dry weight). Oligosaccharides mainly comprised of mannan are capable of interrupting the colonization of the intestinal pathogens so as to improve the intestinal environment. They may act as an antigen to initiate the antibody response directly, and act as an immunostimulatory factor to enhance the humoral and cellular immunity of animals.

By treating the cell wall of microorganisms with a protease and a mannanase, the method of the present invention may extract glucan and mannan simultaneously from the microbial cell wall. The glucan preparation and mannan preparation thus produced may find various applications, for example, used in human food, animal feed, cosmetics, medication and nutrients as an additive, or used together with agriculturally acceptable carriers in plant protective compositions, in combination with agricultural nutrients, herbicides or pesticides.

In the present invention, any suitable microorganism can be used as the source of glucan/mannan, including but not limited to bacteria, fungi and plants such as unicellular algae. For example, the microorganism may be a bacterium, such as *Alkaligenes, Agrobacterium, Cellulomonas* and *Pestalotia;* or a fungus, such as *Aureobasidum, Agaricus, Lentinus, Pleurotus ostreatus, Macrophomopsis, Ganoderma, Schizophylla, Fachyma hoelen, Pestahlia* and *Corioulus*. Non-microbial (such as plant) materials can also be used as the source of glucan/mannan.

In some embodiments, yeasts are used as the source of glucan/mannan. The yeast may be, for example, *Saccharomyces,* such as *Saccharomyces cerevisiae* (including bakers' yeast and brewers' yeast), *Saccharomyces delbrueckii, Saccharomyces rosei, Saccharomyces microellipsodes, Saccharomyces carlsbergensis; Kluyveromyces,* such as *Kluyveromyces fragilis, Kluyveromyces lactis, Kluyveromyces polysporus; Candidas,* such as *Candidas utilis, Candidas albicans, Candidas cloacae, Candidas tropicalis, Candidas guilliermondii; Schizosaccharomyces,* such as *Schizosaccharomyces pombe;* and *Hansenula,* such as *Hansenula wingei, Hansenula arni, Hansenula henricii, Hansenula Americana.*

Preferably, a *Saccharomyces* strain, especially *Saccharomyces cerevisiae*, are used as the source of glucan/mannan in the method of the present invention, which may be the yeast cells, the yeast derivatives such as dry yeast, yeast milk, yeast cell wall etc., or any combination thereof.

In the preparation method of the present invention, the microbial cells are firstly treated by a protease and a mannanase, and then separated based on density. The fraction with higher density (hereinafter referred to as the "heavy phase", such as the precipitate) contains glucan, while the fraction with lower density (hereinafter referred to as the "light phase") contains mannan. Suitable methods for the separation are well known to an ordinary person skilled in the art, including for example centrifugation, in which the speed for centrifugation can vary within a wide range and can be determined by the conventional techniques.

After the centrifugation, the heavy phase and the light phase are collected and dried separately, thereby obtaining the glucan and the mannan preparation. Optionally, the heavy phase and the light phase can be concentrated and then dried separately.

Without wishing to be bound by any theory, the protease treatment and mannanase treatment of the present invention are considered to hydrolyze the proteins and polysaccharides in the microbial cell wall in a large amount, and destroy the structure of the cell wall, so as to expose the glucan, facilitating the extraction of the glucan and mannan.

The proteases suitable for the method of the present invention are well known to those skilled in the art. They are commercially available from certain manufactures, or can be prepared by the skilled person according to conventional methods, including for example extraction, genetic engineering etc. In some embodiments, the protease is an alkaline protease. For example, the protease presents a substantial activity at a pH ranging from pH 7-10, pH 7.5-9.5 or pH 7.8-9.5. Examples of the suitable proteases include but not limited to Subtilisin 147, Subtilisin 309, Subtilisin BPN', Subtilisin Novo, ALCALASE™ (subtilisin), SAVINASE™ (subtilisin), DURAZYM™ (subtilisin) (obtainable from Novozymes); MAXATASE™ (alkaline protease), MAXACAL™ (alkaline protease), PURAFECT™ (alkaline protease), FN2™ (alkaline protease), FN3™ (alkaline protease) (obtainable from Genencor International Inc.), VALIDASE AFP™ (alkaline protease), VALIDASE™ FP500 (alkaline protease), VALIDASE™ FP II (alkaline protease), BROMELAIN™ (alkaline protease) (obtainable from Valley Research, South Bend, IN) or the alkaline protease from Pangbo Biological Engineering Co., Ltd., Nanning, China, or any combination thereof. In the method of the present invention, the amount of the protease can be conventionally determined by an ordinary skilled person in the art, for example 0.0001-10%, 0,001-5%, 0.01-1% or 0.05-0.5% (in dry weight of the yeast material to be treated).

The mannanases suitable for the method of the present invention are well known to those skilled in the art. They are commercially available from certain manufactures or can be prepared by a skilled person according to conventional methods including for example extraction, genetic engineering etc. Suitable mannanases include but not limited to GAMANASE™ (mannanase) (obtainable from Novozymes), PURABRITE ™ (mannanase) (obtainable from Genencor International Inc.) or the mannanase from Pangbo Biological Engineering Co., Ltd., Nanning, China, or any combination thereof In the method of the present invention, the amount of the mannanase can also be conventionally determined by an ordinary skilled person in the art, for example 0.0001-10%, 0.001-8%, 0.01-6%, 0.05-5% or 0.1-3% (in dry weight of the yeast material to be treated).

In some embodiments, the protocol of treating the microbial cells with a protease and a mannanase includes treating the cells with the protease under suitable conditions, and then treating the cells with the mannanase under suitable conditions.

The specific conditions for the enzyme treatment will partially depend on the specific enzymes used. Those skilled in the art can determine the suitable pH, temperature, duration and the suitable amount of enzymes, according to the specific enzymes applied.

In some embodiments, the protease treatment can be carried out at pH 7-10, preferably pH 7.0-9.5, such as pH 7.5-9.0, pH 7.5-9.5, pH 7.0-9.0, pH 7.0-8.8. The temperature for the protease treatment can be for example 10-70 C, such as 20-65 C, 25-65 C, 30-60 C or 35-60 C, 65 or 55 C. The duration can be 1-20 hrs, such as 2-15 hrs, 3-12 hrs, 5-12 hrs etc.

In other embodiments, the mannanase treatment can be carried out at pH 4.0-7.2, such as pH 4.0-7.0, pH 4.5-7.0, pH 4.8-7.0, pH 5.0-7.0 or pH 4.0-6.0, pH 4.0-6.5, pH 4.5-6.0, pH 4.5-6.5, etc. The temperature for the protease treatment can be 10-70 C, such as 20-65 C, 25-60 C, 30-55 C or 35-50 C. The duration can be 4-20 hrs, such as 6-15 hrs, 8-12 hrs etc.

Optionally, a pretreatment, such as heat treatment, lysis or autolysis, can be carried out prior to treating the microbial cells or fraction materials thereof with the protease and mannanase according to the present invention. Autolysis is a process in which the macromolecules are lysed by the microbial endogenous enzymes. Methods for the autolysis of microorganisms are well known in the art. During the lysis or autolysis, exogenous enzymes (e.g., protease) can be additionally added to facilitate the lysis. In an embodiment, the microbial cells (e.g., yeast cells) or their fractions containing the cell wall are formulated into 1-20% aqueous solution, and then reacted for 0.5-3 hrs at 50-100 C. In another embodiment, the microbial cells or their fractions containing the cell wall are formulated into 1-20% aqueous solution, then a protease is added to 0.05%-10% (by weight of the enzyme/the yeast dry matter), and incubated for 5-30 hrs at 35-50 C for the pretreatment. Suitable proteases are known to the skilled one in the art, including for example papain. Such proteases are commercially available, such as from Pangbo Biological Engineering Co., Ltd., Nanning, China, or can be prepared by methods of extraction or genetic engineering.

Therefore, in a particular embodiment, the protease treatment and mannanase treatment can be carried out as follows. The microbial materials (such as the yeast cell wall) are firstly formulated into 1-20% suspension (in weight) with water, and reacted for 0.5-3 hrs at 50-100 C. Then the temperature is adjusted to 10-70 C, and pH is adjusted to 7.0-9.0, and the alkaline protease is added to a final concentration of 0.5-4‰ (the weight of the enzymes/the yeast dry matter) and incubated for 6-10 hrs. Then the pH is adjusted to pH 4.0-7.0, and the mannanase is added to the final concentration of 0.5-4‰ (the weight of the enzymes/the weight of the yeast dry matter) and incubated for 8-12 hrs.

In the present invention, suitable acidic or alkaline substances can be added to adjust the pH values required for the enzymolysis system, including for example sodium hydroxide, potassium hydroxide, sodium carbonate, hydrochloric acid, sulfuric acid, phosphoric acid, citric acid, etc., which are within the capacity of the ordinary skilled person in the art.

In the methods of the present invention, the separation steps may be performed using the conventional separation methods based on density, such as centrifugation. In a preferable embodiment, the separation is performed by using disc separator.

The drying step in the method of the present invention can be performed utilizing any method well known to those skilled in the art, including but not limited to lyophilization, roller drying, spray drying, and film drying. Optionally, the drying step can be performed after a grinding step. In a preferred embodiment, the drying is a spray drying, for example, at 100-180 C. Optionally, concentrations can be performed by the conventional techniques known in the art prior to any drying step.

Preferably, the method of the present invention can be combined with conventional methods for glucan extraction. For example, after the microorganisms are treated by the protease and mannanase and separated, the obtained heavy phase is subsequently treated by alkalis and acids. Since substantial contaminants have been removed by the enzyme treatment, the yield of the method of the present invention is higher than that of the conventional methods utilizing acid and alkali. Furthermore, since the amount of materials to be treated is decreased after the removal of contaminants, the amount of the alkali and acid used is decreased, which leads to a less environmental pollution and a less corrosion of devices.

As is well known to those skilled in the art, suitable alkalis in such a subsequent alkaline treatment include but not limited to sodium hydroxide, potassium hydroxide or the combination thereof, the final concentration of which in the alkali treatment system may be for example 0.5-10%, preferably 1-8%, more preferably 2-6% (w/v). The alkali treatment are generally performed under heated conditions, for example, at the temperature of 50-120 C, such as 50-120 C, 60-110 C, 65-100 C, 70-95 C, for an appropriate period of time, such as 1-20 hrs, 2-15 hrs, 2-10 hrs or 2-8 hrs. Preferably, the heavy phase treated with alkali is separated, for example by centrifugation. In an embodiment, the alkali treatment is performed as follows. The heavy phase obtained by the alkali treatment and separation are optionally concentrated and/or dried, then formulated with water to the concentration of 0.2-20%, such as 0.5-15% or 1-10%. The alkali is added up to the final concentration of 0.5-10%, preferably 1-8%, most preferably 2-6% (w/v), and preferably heated up to 70-100 C and incubated for 1-4 hrs. Optionally, the system treated by the alkali is separated, for example by centrifugation.

The heavy phase obtained by the alkali treatment can be further treated by acids. Suitable acids are well known to the ordinary skilled in the art, including but not limited to sulfuric acid, acetic acid, hydrochloric acid or phosphoric acid, or any combination thereof. In an embodiment, the heavy phase that is obtained by the alkali treatment and optionally concentrated and/or dried is formulated with water to the concentration of 1-10%, adjusted to pH 3-5 with an acid, heated to 60-100 C and incubated for 0.5-5 hrs, such as 1-4 hrs. During the incubation process, stirring can be carried out.

After the system treated by an alkali and an acid is separated, for example by centrifugation, the obtained heavy phase is concentrated and/or dried, thereby obtaining a yeast glucan preparation. If necessary, the heavy phase obtained from the system treated by an alkali and an acid may be separated by centrifugation for several times, for example, added up with water and separated again by centrifugation. Then, the final heavy phase is concentrated and/or dried as described above regarding the product treated by enzymes and separated.

A glucan preparation with a content higher that 70% and a mannan preparation with a content higher that 40% can be prepared from yeast cells, according to the method of the present invention. The extraction rate of the present method is 60-95%. The method of the present invention can be carried out under mild conditions with excellent stability, and is suitable for industrial production.

The contents of the glucan and mannan in the final preparation can be determined by various techniques well known to those skilled in the art, such as phenol-sulfuric acid method, DNS, Fehling's titration, chromatography, etc.

The present invention relates further to the mannan preparation and glucan preparation prepared according to the method of the present invention, which can be administered alone or in combination with edible, pharmaceutically acceptable or cosmetically acceptable carriers or excipients. Therefore, they can be formulated in the form of solution, particles, tablets, pills and emulsions, etc. Their effective amount and method for preparation can be determined by those skilled in the art through conventional methods.

The mannan preparation and glucan preparation prepared according to the method of the present invention can be applied to various applications. For example, the yeast mannan, which is water soluble polysaccharide and can be supplemented to various food, nutrients, feed, and cosmetics, plays a role in enhancing immunity and adsorbing toxins, etc.

Features and various aspects of the present invention are exemplified by the following specific Examples. Unless specifically indicated, the protocols and reagents used in the present invention are well-known methods and reagents. It should be noted that, these Examples are illustrative and do not limit the scope of the present invention. The spirit and scope of the present invention are restricted by the claims. Alternations or modifications on the enzyme treatment conditions, the acid and alkali treatment process, the separation conditions may be made without departing from the spirit and scope of the present invention, thus are encompassed by the scope of the invention.

EXAMPLES

In the following examples, the percentage of the added enzymes is based on the ratio of the enzymes to the dry weight of the original material (e.g., the percentage of the enzyme to the dry weight of the yeast cells). The alkaline protease and mannanase used in the following Examples are obtained from Pangbo Biological Engineering Co., Ltd., Nanning, China.

Example 1

Preparation of Mannan a) 500 kg baker's yeast (highly active dry yeast, Angel Yeast Co., Ltd, China) was formulated with water into a 10% (w/w) suspension, incubated for 1 hr at 90 C, adjusted to 60 C, and adjusted to pH 7.0 with hydrochloric acid or sodium hydroxide. The alkaline protease was added to 3‰, and incubated for 8 hrs. Then, the pH was adjusted to 5.0 with hydrochloric acid, the mannanase was added to 3‰, and incubated for 10 hrs.

b) Separation at 6000 g by disc separator (Jiangsu Juneng Machinery Co., Ltd, China). The heavy phase and light phase were collected separately.

c) The light phase obtained from b) was concentrated by vacuum concentration, and was spray dried at 180 C, obtaining the mannan preparation as pale yellow powder. The mannan content was 40% as determined by phenol-sulfuric acid method.

Example 2

Preparation of Mannan a) 500 kg yeast cell wall prepared from the baker' yeast by autolysis was formulated with water into a 3% (w/w) suspension, incubated for 3 hrs at 100 C, cooled to 50 C, and adjusted to pH 9.0 with sodium hydroxide. The alkaline protease was added to 1‰, and incubated for 10 hrs. Then, the pH was adjusted to 4.0 with hydrochloric acid or sodium hydroxide, the mannanase was added to the final concentration of 4‰ and incubated for 12 hrs at 50 C.

b) Separation at 3000 g using disc separator. The heavy phase and light phase were collected separately.

c) The light phase obtained from b) was concentrated by vacuum concentration, and was spray dried at 160 C, obtaining a mannan preparation as pale yellow powder. The mannan content was 42% as determined by phenol-sulfuric acid method.

Example 3

Preparation of Mannan a) 500 kg yeast cell wall prepared from the baker' yeast by autolysis was formulated with water into 20% (w/w) suspension, incubated for 2 hrs at 50 C, cooled to 10 C, and adjusted to pH 8.0 with sodium hydroxide. The alkaline protease was added to 4‰, and incubated for 10 hrs at 50 C. Then, the pH was adjusted to 6.0 with hydrochloric acid or sodium hydroxide, the mannanase was added to 2‰ and incubated for 10 hrs at 50 C.

b) Separation at 10000 g using disc separator. The heavy phase and light phase were collected separately.

c) The light phase obtained from b) was concentrated by vacuum concentration, and was spray dried at 180 C, obtaining a mannan preparation as pale yellow powder. The mannan content was 44% as determined by phenol-sulfuric acid method.

Example 4

Preparation of Mannan a) 500 kg yeast cell wall prepared from the baker' yeast by autolysis was formulated with water into a 1% (w/w) suspension, incubated for 0.5 hr at 80 C, cooled to 70 C, and adjusted to pH 8.0 with sodium hydroxide. The alkaline protease was added to 0.5‰, and incubated for 6 hrs at 70 C. Then, the pH was adjusted to 7.0 with hydrochloric acid, the mannanase was added to 0.5‰ and incubated for 8 hrs at 70 C.

Steps b) and c) were performed as in Example 4, obtaining the mannan content of 42%.

Example 5

Preparation of Glucan

Steps a) and b) were performed as in Example 1;

c) The heavy phase obtained from b) was concentrated by vacuum concentration, and was spray dried, obtaining the glucan preparation as powder. The glucan content was 45% as determined by phenol-sulfuric acid method.

Example 6

Preparation of Glucan

Steps a) and b) were performed as in Example 1;

c) The heavy phase obtained from b) was formulated with water to a 5% suspension. NaOH was added to the final concentration of 5%, incubated for 3 hrs at 90 C with continuous stirring, and cooled to 60 C;

d) Separation at 8000 g using disc separator. The heavy phase and light phase were collected separately;

e) The heavy phase obtained from d) was formulated with water to a 5% suspension, adjusted to pH 4.5 with concentrated sulfuric acid, incubated for 1 hr at 90 C with continuous stirring, and cooled to 50 C;

f) Separation at 8000 g using disc separator. The light phase was discarded. The heavy phase was supplemented with water to the volume prior to the separation, and separated again. The separation was repeated four times;

g) The heavy phase obtained from f) was spray dried at 160 C, obtaining the glucan preparation as powder. The glucan content was 85% as determined by phenol-sulfuric acid method.

Example 7

Preparation of Glucan

Steps a) and b) were performed as in Example 1;

c) The heavy phase obtained from b) was formulated with water to a 8% suspension. KOH is added to the final concentration of 2%, incubated for 3 hrs at 70 C with continuous stirring, and cooled to 50 C;

d) Separation at 8000 g using disc separator. The light phase was discarded. The heavy phase was supplemented with water to the volume prior to the separation, and separated again using disc separator. The separation was repeated 4 times;

e) the heavy phase obtained from d) was formulated with water to a 5% suspension, adjusted to pH 3.5 with acetic acid, incubated for 1.5 hrs at 100 C with continuous stirring, and cooled to 60 C;

f) Separation at 6000 g using disc separator. The light phase was discarded. The heavy phase was supplemented with water to the volume prior to separation, separated again using disc separator. The separation was repeated five times;

g) The final heavy phase obtained from f) was spray dried at 100 C, obtaining the glucan preparation as powder. The glucan content was 70% determined by phenol-sulfuric acid method.

Example 8

Preparation of Mannan and Glucan a) The baker's yeast (highly active yeast, Angel Yeast Co., Ltd, China) was formulated into a 15% suspension;

b) To the suspension papain (Pangbo Biological Engineering Co., Ltd., Nanning, China) was added to 0.5%, incubated for 20 hrs at 45 C with continuous stirring;

c) The suspension was heated to 90 C for 1 hr, centrifugated at 6000 g using a centrifuge, and the heavy phase was collected;

d) The heavy phase from c) was formulated with water into a 8% suspension;

e) The suspension of d) was heated to 100 C for 1 hr, cooled to 60 C, and adjusted to pH 9.5 with sodium hydroxide. Alkaline protease was added to 4‰, and incubated for 8 hrs. Then, the pH was adjusted to 7.0, mannanase was added to the final concentration of 0.4‰, and incubated for 8 hrs at 50 C;

f) Separation at 10000 g using a disc separator, and the heavy phase and light phase were collected separately;

g) The light phase from f) was spray dried, obtaining the mannan preparation as powder. The mannan content was 45% as determined by phenol-sulfuric acid method;

h) The heavy phase from f) was formulated with water into a 5% suspension. KOH was added to the final concentration of 3%, incubated for 3 hrs at 95 C, cooled to 60 C, and centrifuged at 6000 g using a disc separator. The heavy phase was collected;

i) The heavy phase from h) was formulated with water into a 5% suspension, adjusted to pH 4.0 with hydrochloric acid, incubated for 1 hr at 85 C, and centrifugated at 6000 g using a disc separator. The heavy phase was collected;

j) The heavy phase from i) was spray dried, obtaining the glucan preparation as powder. The glucan content was 75%.

Example 9

Preparation of Mannan and Glucan a) The baker's yeast was formulated into a 12% suspension;

b) To the suspension papain (Pangbo Biological Engineering Co., Ltd., Nanning, China) was added to the final concentration of 1%, incubated for 18 hrs at 50 C with continuous stirring;

c) The suspension was heated to 85 C for 1 hr, and centrifuged at 10000 g using a centrifuge. The heavy phase was collected;

d) The heavy phase from c) was formulated with water into a 10% suspension;

e) The suspension from d) was heated to 100 C for 2 hrs, cooled to 60 C, and adjusted to pH 7.5 with hydrochloric acid or sodium hydroxide. The alkaline protease was added to 2‰, and incubated for 10 hrs;

f) Separation by centrifuge at 6000 g. The heavy phase and light phase were collected separately;

g) The light phase from f) was spray dried, obtaining the mannan preparation as powder. The mannan content was 35%;

h) The heavy phase from f) was formulated with water into a 5% suspension. KOH was added to the final concentration of 3%, incubated for 3 hrs at 95 C, cooled to 60 C, and centrifugated at 6000 g. The heavy phase was collected;

i) The heavy phase from h) was formulated with water into a 5% suspension, adjusted to pH 4.0 with hydrochloric acid, incubated for 1 hr at 85 C, and centrifugated at 6000 g. The heavy phase was collected;

j) The heavy phase of i) was spray dried, obtaining the glucan preparation as powder. The glucan content is 60%.

The method of the present invention presents one or more advantages as follows: milder reaction conditions, simpler protocols, excellent stability, higher yield, less pollution, suitable for large scale industrial production and obtaining mannan at the same time.

Although the present invention has been detailed with the general description and the above specific embodiments, it is apparent to those skilled in the art that changes or modifications can be made based on the present invention. Therefore, such changes or modifications that do not depart from the spirit of the present invention are within the scope sought to be protected by the invention.

The invention claimed is:

1. A method for preparing a glucan preparation, comprising the steps of:
    a) treating the cells of a microorganism with a protease and a mannanase;
    b) separating the mixture obtained from step a) into a heavy phase and a light phase;
    c) treating the heavy phase obtained from step b) with an alkali and an acid sequentially, and separating the treated heavy phase into a heavy phase and a light phase; and
    d) drying the heavy phase obtained from step c), obtaining the glucan preparation.

2. A method for preparing a glucan and mannan preparation, comprising the steps of:
    a) treating the cells of a microorganism with a protease and a mannanase;
    b) separating the mixture obtained from step a) into a heavy phase and a light phase;
    c) treating the heavy phase obtained from step b) with an alkali and an acid sequentially, and separating the treated heavy phase into a heavy phase and a light phase;
    d) drying the heavy phase obtained from step c), obtaining the glucan preparation; and
    e) drying the light phase obtained from step b), obtaining the mannan preparation.

3. The method of claim 1 or 2, further including a pretreatment that lyses or autolyses the cells of the microorganism prior to step a).

4. The method of claim 1 or 2, wherein the protease is an alkaline protease.

5. The method of claim 4, wherein the protease treatment is performed at pH 7-10 10-70° C.

6. The method of claim 1 or 2, wherein the mannanase is selected from the group consisting of GAMANASE ™ (mannanase) (Novozymes), PURABRITE™ (Genencor International Inc.), the mannanase from Pangbo Biological Engineering Co., Ltd., Nanning, China, and combinations thereof.

7. The method of claim 6, wherein the mannanase treatment is performed at pH 4.0-7.2 and a temperature of 10-70° C.

8. The method of claim 1 or 2, wherein the separation is performed utilizing disc separator.

9. The method of claim 1 or 2, wherein the cells of the microorganism are selected from the group consisting of bacteria, fungi and plant cells.

10. The method claim 1 or 2, wherein the microorganism is a yeast cell.

11. The method of claim 1 or 2, wherein the alkali treatment is performed utilizing an alkali with the final concentration of 0.5-10%-at the temperature of 50-120° C.

12. The method of claim 1 or 2, wherein the acid treatment is performed utilizing an acid to adjust the reaction system to pH 3-5, at the temperature of 60-100° C.

13. The method of claim 1 or 2, wherein the reaction system is separated by centrifugation after the alkali treatment and before the acid treatment, and the obtained heavy phase is optionally concentrated or dried prior to the acid treatment.

* * * * *